United States Patent [19]

Small

[11] 4,120,819
[45] Oct. 17, 1978

[54] METHOD FOR PLATINUM OR PALLADIUM CATALYST REACTIVATION

[75] Inventor: Robert James Small, Worthington, Ohio

[73] Assignee: Ashland Oil, Inc., Ashland, Ky.

[21] Appl. No.: 833,506

[22] Filed: Sep. 15, 1977

[51] Int. Cl.$^2$ .................... B01J 23/96; B01J 21/20; C07C 103/32
[52] U.S. Cl. .................................... 252/413; 252/415; 252/416; 260/561 H
[58] Field of Search ............... 252/413, 415, 416, 414; 260/561 H

[56] References Cited

U.S. PATENT DOCUMENTS

| | | | |
|---|---|---|---|
| 3,016,354 | 1/1962 | Hindin et al. | 252/413 |
| 3,488,295 | 1/1970 | Sennewald | 252/415 |
| 4,045,484 | 8/1977 | Maiz, Jr. et al. | 260/561 H |

Primary Examiner—P. E. Konopka

[57] ABSTRACT

Palladium or platinum catalyst values poisoned in course of catalyzing the reductive alkylation of an acid hydrazide are essentially completely reactivated by treating the spent catalyst values with a dilute aqueous solution of a lower monocarboxylic acid or a mineral acid and contacting the resultant slurry with oxygen gas or a labile oxygen containing compound.

5 Claims, No Drawings

METHOD FOR PLATINUM OR PALLADIUM CATALYST REACTIVATION

BACKGROUND OF THE INVENTION

1. Field of the Invention

This invention relates to a method for reactivating or regenerating a noble metal catalyst by oxidation treatment.

2. Description of the Prior Art

Mono methyl hydrazine (MMH) and unsymmetrical dimethylhydrazine (UDMH), due to the ability of these compounds to provide hypergolic ignition upon contact with a strong oxidizer, represent important liquid propellant fuels, particularly for space vehicles. Although there are several routes available for the production of these compounds, all, however, involve problems of one type or another.

For example, the most expedient process for producing UDMH consists of hydrogenating nitrosodimethylamine in turn obtained by nitrosating dimethylamine. This process, however, has been banned for all practical purposes because of the extremely potent carcinogenic nature of the nitrosodimethylamine intermediate. A currently practiced process for producing MMH is in accordance with a modified Raschig synthesis involving the in situ generation of mono-chloramine and subsequent reaction with monomethyl amine. The principal disadvantage of this process is that it is very energy intensive.

The remaining process commercially applicable for producing UDMH as well as MMH, and the process to which the present invention relates, consists of the reductive alkylation of an acid hydrazide with formaldehyde in the presence of hydrogen and a suitable hydrogenation catalyst and subsequent base hydrolysis or hydrozinolysis of the resultant alkylate. In order to realize an acceptable yield of product in accordance with the foregoing process, it is necessary to use either palladium or platinum as the catalyst. Unfortunately, however, the reaction environment is such that the indicated catalysts are prone to become poisoned and lose substantially all activity after completing an initial alkylation sequence. It is therefore the object of this invention to provide a facile method for restoring the activity of said catalyst values to essentially their initial pristine level following each use thereof as aforesaid.

SUMMARY OF THE INVENTION

In accordance with the present invention, a method is provided for reactivating palladium or platinum catalyst values which have become poisoned in effecting the reductive alkylation of an acid hydrazide with formaldehyde. The method involves the slurrying of the spent catalyst values with a dilute aqueous solution of a lower monocarboxylic acid or a mineral acid and intimately contacting the slurry with a free oxygen containing gas or a labile oxygen containing compound.

The optimum yields that can be realized in the aforesaid reductive methylation process using fresh catalyst are in the neighborhood of 80 percent. Reuse of the catalyst as such leads to highly erratic results and a yield of as low as 10-20% can be normally expected. However, the catalyst treated in the manner outlined above following each alkylation run permits almost an optimum yield for carrying out an indefinite series of separate operations.

DESCRIPTION OF THE PREFERRED EMBODIMENT

For the purpose of describing the implementation of the present invention, such will be illustrated in context of the process for preparing UDMH wherein acetyl hydrazine is reacted with formaldehyde under hydrogen in the presence of palladium on carbon catalyst. This process will be adequately exemplified in the working example to follow. However, further details concerning this procedure, particularly as to how to achieve optimum yield of product based on the minimum applicable usage of catalyst, can be found in Belgium Pat. No. 839664.

In accordance with the improvement provided by this invention, spent catalyst is first recovered from an alkylation run, preferably by filtering. The wet catalyst is charged as such to a dilute aqueous solution of either a lower monocarboxylic acid or a mineral acid. The preferred acid is acetic; although formic, propionic and like lower monobasic acids can be used. Applicable mineral acids include hydrochloric, sulfuric, nitric and phosphoric.

The concentration of the acid solution, particularly that of the acetic, is normally about 10 wt. %. This concentration can be varied, especially upwardly, but no particular advantage is to be gained in terms of accelerating the purification treatment involved. The wet catalyst in the form of 5% palladium or platinum on a carbon support is slurried with any of the aforementioned aqueous solutions on the basis of about 1 part by weight of the supported catalyst per 20 parts of the acid solution. This ratio is not critical but merely represents the preferred relationship.

In the preferred mode of treating the slurried catalyst, oxygen or a free oxygen containing gas; e.g., air, is introduced into the slurry by sparging. Sparging with air at room temperature for an extended period of about 8 to 16 hours represents the preferred practice. However, the same results can be achieved in a shorter treating period by charging a labile oxygen containing compound and stirring the slurry. Particularly exemplary of the latter type compounds is hydrogen peroxide.

The following working example will serve to illustrate the best mode contemplated for carrying out the invention. All percentages referred to therein not otherwise indicated are by weight.

EXAMPLE

A stock 2.5 kg mole solution of acetyl hydrazine was prepared by charging into a suitable reaction vessel 114.6 kg of ethyl acetate and 66.6 kg of 54% aqueous hydrazine. The reaction mixture was heated with stirring at 110° C. for 5.5 hours at a pressure of 2 kg/cm². Following completion of the reaction, the acetyl hydrazine solution was cooled and stored at room temperature.

A series of five reductive methylation runs were carried out using in each instance a 34.2 kg (0.49 kg mole) quantity of the acetyl hydrazine stock solution. The pH of each charge of the stock solution was adjusted to 6.5–7.0 with glacial acetic acid. In the first run, 638 gm of fresh 5% Pd/C (50% wet) were charged to the reactor. The reactor was pressurized at 11 kg/cm² with hydrogen and the reaction mixture heated to 80° C. with stirring. Methyl Formcel in the amount of 26.3 kg containing 2.5% acetic acid was uniformly pumped into the reactor during a 5 hour period. Following each run in the manner outlined, the dimethyl acetyl hydrazine solution was filtered to recover the catalyst for use in the succeeding run. Likewise in each run an aliquot of the dimethyl acetyl hydrazine solution was stripped of solvents and hydrolyzed with a 100% excess of 50% caustic solution. The individual yields of the unsymmetrical dimethyl hydrazine (UDMH) was determined by GLC analysis. Purity of product for all runs was determined to be in the order of 99+%.

Following the initial run and the subsequent runs tabulated below in Table I, the catalyst was removed from a plate and frame filter press and added to a solution of water (5.7 kg) and acetic acid (0.6 kg) in an open tank provided with an air sparge line and agitator. Air was sparged through the slurry for varying periods ranging from 8 to 16 hours. Following this treatment the catalyst was recovered by vacuum filtering. In the second and subsequent runs, a 10% (63 gm) charge of fresh catalyst was added to compensate for handling losses encountered in the purification treatment. The results obtained in terms of yield of UDMH are given in the following Table I.

TABLE I

| Regeneration of Catalyst With Air | |
|---|---|
| Run No. | Yield % (UDMH) |
| 1 | 77 |
| 2 | 77 |
| 3 | 74 |
| 4 | 76 |
| 5 | 76 |

What is claimed is:

1. In a process for the reductive alkylation of an acid hydrazide wherein the hydrazide is reacted with formaldehyde in the presence of hydrogen and palladium or platinum catalyst supported on carbon; the improvement of regenerating said catalyst by recovering same from the reaction mixture, slurrying with a dilute aqueous solution of a lower monobasic carboxylic acid or a mineral acid, and thereupon intimately contacting said slurry with a free oxygen containing gas or a labile oxygen containing compound to restore the catalyst activity to essentially its initial level, and removing said regenerated catalyst from said slurry.

2. The improvement in accordance with claim 1 wherein said free oxygen containing gas is air.

3. The improvement in accordance with claim 2 wherein said acid is selected from the group consisting of formic, acetic, hydrochloric, sulfuric, nitric and phosphoric.

4. The improvement in accordance with claim 3 wherein said acid is acetic.

5. The improvement in accordance with claim 4 wherein said catalyst is palladium on carbon support.

* * * * *